United States Patent [19]

Gregory et al.

[11] Patent Number: 5,262,179
[45] Date of Patent: Nov. 16, 1993

[54] NON-EFFERVESCENT IBUPROFEN COMPOSITIONS

[75] Inventors: Stuart P. Gregory, Mulgrave; Alexander J. Jozsa, Wantirna South; Robert E. Kaldawi, Ascot Vale, all of Australia

[73] Assignee: Nicholas Kiwi Pty Ltd., Victoria, Australia

[21] Appl. No.: 905,509

[22] Filed: Jun. 26, 1992

Related U.S. Application Data

[63] Continuation of Ser. No. 580,934, Sep. 12, 1990, abandoned.

[30] Foreign Application Priority Data

Sep. 13, 1989 [GB] United Kingdom ............... 8920693

[51] Int. Cl.$^5$ ............................................. A61K 9/14
[52] U.S. Cl. ................................ 424/489; 424/441; 424/44; 514/974; 514/970
[58] Field of Search .............. 424/489, 44, 441; 514/974, 970, 557, 58

[56] References Cited

U.S. PATENT DOCUMENTS

| | | | |
|---|---|---|---|
| 4,788,220 | 11/1988 | Mody et al. | 424/488 |
| 4,859,704 | 8/1989 | Haas | 424/486 |
| 4,861,797 | 8/1989 | Haas | 514/557 |
| 4,975,465 | 12/1990 | Motola et al. | 514/557 |
| 5,019,563 | 5/1991 | Hunter et al. | 514/58 |

FOREIGN PATENT DOCUMENTS

| | | |
|---|---|---|
| 0203768 | 12/1986 | European Pat. Off. |
| 0228164 | 7/1987 | European Pat. Off. |
| 63-198620 | 8/1988 | Japan |
| WO8903210 | 4/1989 | PCT Int'l Appl. |
| 2189994 | 11/1987 | United Kingdom |
| 2193093 | 2/1988 | United Kingdom |

*Primary Examiner*—Thurman K. Page
*Assistant Examiner*—William E. Benston
*Attorney, Agent, or Firm*—Cushman, Darby & Cushman

[57] ABSTRACT

The unpleasant taste of water-soluble ibuprofen salts in aqueous solution is masked by incorporating in the solution a taste-masking amount of an alkali metal bicarbonate, alkali metal monohydrogen phosphate or alkali metal tribasic citrate. Preferably, the taste-masking compound is an alkali metal bicarbonate, especially sodium bicarbonate.

21 Claims, No Drawings

NON-EFFERVESCENT IBUPROFEN COMPOSITIONS

This is a continuation of U.S. patent application Ser. No. 07/580,934, filed on Sep. 12, 1990, which was abandoned upon the filing hereof.

The present invention relates to non-effervescent water-soluble compositions containing ibuprofen in the form of a water-soluble salt thereof. In particular, the invention provides non-effervescent water-soluble compositions of water-soluble ibuprofen salts in which the unpleasant taste of the salt is masked.

Ibuprofen (ie. 2-(4-isobutylphenyl) propionic acid) is well known as a therapeutic agent having analgesic, anti-inflammatory and antipyretic activity. It is extensively used as an alternative to aspirin (i.e. acetylsalicylic acid) and paracetamol (ie. acetaminophen) in the treatment of pain, such as headache, toothache and especially when associated with inflammation in, for example, rheumatic disease. However, ibuprofen is water-insoluble and often causes gastric irritation when administered in solid or suspended form, especially in the doses required to treat rheumatic disease. Only a few salts of ibuprofen are water-soluble and these include the alkali metal salts and amino acid salts. However, solutions of water-soluble ibuprofen salts have an unpleasant burning taste and, for that reason, their use generally has been avoided. Many attempts have been made to improve the solubility and taste of ibuprofen, especially in its free acid form.

GB-A-2189994 discloses that the low water-solubility of ibuprofen can be overcome by formulation into an effervescent composition consisting of 9 to 17 weight percent ibuprofen; 17 to 33 weight percent arginine or an arginine/lysine mixture containing up to 40 weight percent lysine; 20 to 35 weight percent sodium or potassium bicarbonate; and 25 to 40 weight percent sodium or potassium bitartrate. The presence of arginine is essential and it appears that the ibuprofen must be present as the free acid. In particular, it is stated that arginine and lysine salts of ibuprofen cannot be used because they do not result in the complete dissolution of the ibuprofen. No other ibuprofen salts are referred to.

EP-A-0203768 discloses effervescent compositions of a pre-blended mixture of granulated therapeutic agent and effervescent system component. The therapeutic agent is required to have a particle size of 100 to 600 micrometres and the effervescent system component is required to have a particle size of 50 to 600 micrometres. Ibuprofen is included amongst numerous specified therapeutic agents and sodium, potassium and ammonium bicarbonate are included amongst the specified effervescent system components. However, there is no exemplification of any ibuprofen-containing composition and there is no reference to the use of ibuprofen salts.

EP-A-0228164 discloses effervescent ibuprofen-containing compositions which provide an improved suspension of ibuprofen or a salt thereof when added to water. The composition includes a pharmaceutically acceptable surfactant and a pharmaceutically acceptable water-insoluble hydrophilic polymer. Exemplified polymers include starch and derivatives thereof, cellulose and derivatives thereof; cross-linked polyvinylpyrrolidone and alginic acid. The preferred polymers are microcrystalline cellulose and croscarmellose sodium. Specified base components of the effervescent couple include sodium and potassium bicarbonate. The amounts of the components of the effervescent couple are generally chosen so that the pH of the resultant aqueous suspension is below 7.0, preferably 3.0 to 4.0. Free ibuprofen is preferred but reference is made to the use of the sodium or potassium salt. When the ibuprofen is in the form of such a water-soluble salt, the salt reacts with the acid component of the effervescent couple to cause ibuprofen to precipitate on addition of the composition to water.

GB-A-2193093 discloses water-soluble ibuprofen compositions containing 33-46 weight percent free ibuprofen, 34-51 weight percent L-arginine and 9-29 weight percent sodium bicarbonate. The molar ratio of L-arginine to ibuprofen is required to be in the range 1.1:1 to 1.5:1 and the weight ratio of sodium bicarbonate to ibuprofen is required to be in the range 0.25:1 to 0.75:1. In an acknowledgement of prior art, GB-A-2193093 refers to the good water-solubility of sodium ibuprofen but teaches against the use of this salt in an oral preparation. In particular, it is stated that:

"Ibuprofen sodium salt is one of few salts with a good solubility in water, but it is not very suitable for an oral preparation because it gives solutions having a pH which produces gastrointestinal damage."

Example 13 of GB-A-2193093 discloses a comparative granulate containing arginine ibuprofen (37 wt %), sodium bicarbonate (10 wt %) and saccharose (46 wt %). The mole ratio of sodium bicarbonate to arginine ibuprofen is 1.2:1. Insoluble ibuprofen is formed on dissolution of the granulate in water resulting in a preparation which is stated to be unacceptable both for taste and local tolerability.

JP-A-63198620 discloses non-effervescent ibuprofen compositions containing an antacid and/or mucous membrane covering agent to reduce the risk of digestive disorders. The antacid and/or mucous membrane covering agents specified include sodium bicarbonate but there is no exemplification of compositions including sodium bicarbonate. Further, there is no reference to the use of an ibuprofen salt or to masking the taste of the ibuprofen.

WO 89/03210 discloses that clear, stable and palatable liquid ibuprofen compositions can be obtained by dispersing and suspending, or dissolving, ibuprofen or salts or esters thereof in an aqueous medium containing a methylcellulose composition. A flavouring agent, especially a sweetening agent, can be present to mask the bitter taste of ibuprofen. Optionally, a bicarbonate, preferably potassium bicarbonate, is present in the aqueous medium to assist dispersion of the ibuprofen. A flavouring agent, preferably sucrose, can be added to mask the taste of the ibuprofen. There is no reference to the use of a bicarbonate with an ibuprofen salt or to non-aqueous preparations containing both ibuprofen and bicarbonate. In the compositions of the Examples, the amount by weight of sucrose is about four times that of potassium bicarbonate except in the composition of Example 6 which contains no bicarbonate. The mole only ratio of bicarbonate to ibuprofen disclosed is a 1.2 (Examples 1,4 & 5), and.

It has now surprisingly been found that the inclusion of sodium bicarbonate in a sufficient amount in a non-effervescent water-soluble composition containing a water-soluble ibuprofen salt will mask the taste of ibuprofen in an aqueous solution of the composition. Further, it has been found that potassium bicarbonate, but not ammonium bicarbonate, can be used as an alternative to sodium bicarbonate. It also has been found that the corresponding monohydrogen phosphate and tribasic citrate salts have a similar, but less effective, taste-masking effect.

According to a first aspect of the present invention, there is provided a non-effervescent water-soluble composition comprising a water-soluble ibuprofen salt, characterised in that the composition contains a taste-masking compound selected from alkali metal bicarbonates, alkali metal monohydrogen phosphates and alkali metal tribasic citrates in an amount sufficient to mask the taste of the ibuprofen salt in an aqueous solution of the composition.

In a second aspect, the invention provides the use of alkali metal bicarbonates, alkali metal monohydrogen phosphates and alkali metal tribasic citrates to mask the taste of a water-soluble ibuprofen salt in an aqueous solution thereof.

In a third aspect, the invention provides a method of masking the taste of a water-soluble ibuprofen salt in aqueous solution by incorporating into the solution a taste-masking compound selected from alkali metal bicarbonates, alkali metal monohydrogen phosphates and alkali metal tribasic citrates in a taste-masking amount.

Usually, the ibuprofen salt will be the potassium or, preferably, sodium salt although other water-soluble ibuprofen salts, such as an amino acid, eg. arginine or lysine, salt can be used. If required, the salt can be formed in situ in the aqueous solution.

Alkali metal bicarbonates are much preferred as the taste-masking compounds. Alkali metal monohydrogen phosphates and, especially, tribasic citrates also have a significant taste-masking effect. However, alkali metal monobasic and dibasic citrates and alkali metal dihydrogen phosphates are unsatisfactory because their pKa values are sufficiently low that they cause ibuprofen to be precipitated from an aqueous solution of water-soluble ibuprofen salts. Alkali metal carbonates and tribasic phosphates cannot be used because, in potential taste-masking amounts, the resultant aqueous solution has an unacceptably high pH for oral administration.

Usually, the alkali metal anion of the taste-masking compound will be potassium or, preferably, sodium. In the context of this Application, the term "alkali metal" applied to the taste masking compound does not include ammonium. The use of ammonium bicarbonate results in an unpalatable aqueous solution.

The amount of taste-masking compound required will depend upon the amount of ibuprofen salt present in the composition and the extent to which the taste of that salt is to be masked. Usually, the taste-masking compound will be present in an excess by weight of the ibuprofen salt calculated as free ibuprofen. In case of the taste-masking by bicarbonates, the molar ratio of the bicarbonate to the ibuprofen salt is suitably between 1:4 and 12:1. Preferably, the molar ratio is between 3:4 and 9:1, especially 4:1 to 9:1 for sodium bicarbonate and 3:4 to 9:2 for potassium bicarbonate. In the case of taste-masking by alkali metal mono-hydrogen phosphates, the molar ratio of the mono-hydrogen phosphate to the ibuprofen salt is suitably between 3:4 and 7:1. Preferably, the molar ratio is between 5:2 and 6:1, especially 5:2 to 5:1 for the disodium salt and 7:2 and 6:1 for the dipotassium salt. In the case of taste-masking by alkali metal tribasic citrates, the molar ratio of the tribasic citrate to the ibuprofen salt is suitably between 1:3 and 3:1. Preferably, the molar ratio is between 2:3 and 4:3, especially 3:4 to 4:3 for the trisodium salt and 2:3 to 4:3 for the tripotassium salt.

The composition of the invention usually will be in the form of a free-flowing powder suitably contained in unit dose sachets. However, the composition could be in any other form, such as a water-soluble tablet, suitable for dissolution in water, or syrup. In the case of a solid water-soluble formulation such as a tablet, the composition can include a small amount of an effervescent couple to assist dispersion of the tablet on addition to water. Said amount of effervescent couple is well below that required for the composition to be classified as an effervescent composition, in which there is sustained and substantial evolution of carbon dioxide. The composition can also contain conventional additives such as sweeteners, eg. aspartame and/or cyclamates; disintegrants; glidants; lubricants; and bulking agents, eg. fructose, sorbitol, dextrates or sucrose.

Unit doses of the compositions of the present invention usually will contain ibuprofen salt in an amount equivalent to a conventional oral unit dose of ibuprofen, usually 200 or 400 mg (calculated as free ibuprofen).

The invention is illustrated in the following non-limiting examples. In the Examples, the sodium ibuprofen used was the dihydrate salt (molecular weight 264.3) and hence 512 mg of this salt corresponds to 400 mg ibuprofen.

EXAMPLE 1

A non-effervescent, dry powdered sodium ibuprofen formulation was prepared by mixing together the following ingredients and filling the mixture into sachets containing the equivalent of 400 mg free ibuprofen:

| Ingredient | mg/sachet | % w/w | purpose |
|---|---|---|---|
| sodium ibuprofen | 512 mg | 19.7% | active compound |
| sodium bicarbonate | 700 mg | 26.9% | taste modifier (and buffer) |
| dextrose | 1300 mg | 50.0% | bulking agent |
| sodium saccharin | 50 mg | 1.9% | sweetener |
| blackcurrant flavour | 40 mg | 1.5% | flavour |
| TOTAL | 2,602 mg | 100.0% | |

(Mole ratio taste-masking compound: ibuprofen salt=4.3:1)

The contents of each sachet readily dissolved in 100 ml water and the objectionable taste and burning sensation normally associated with sodium ibuprofen were substantially undetectable in the resulting solution by most patients.

EXAMPLE 2

The procedure of Example 1 was repeated but using only 500 mg/sachet sodium bicarbonate and increasing the amount of dextrose to 1500 mg/sachet to compensate for this decrease. (Mole ratio taste-masking compound: ibuprofen salt=3.1:1.) In this case, the resulting aqueous solution was not as acceptable as that of Example 1 but was a substantial improvement over compositions not containing sodium bicarbonate. Most of the objectionable taste was removed but a burning sensation was still detectable.

EXAMPLE 3

A non-effervescent, dry powdered sodium ibuprofen formulation was prepared by mixing together the following ingredients and filling the mixture into sachets containing the equivalent of 200 mg free ibuprofen:

| Ingredient | mg/sachet | % w/w | purpose |
|---|---|---|---|
| sodium ibuprofen | 256 mg | 15.5% | active compound |
| sodium bicarbonate | 700 mg | 42.4% | taste modifier (and buffer) |
| dextrose | 650 mg | 39.4 | bulking agent |
| sodium saccharin | 25 mg | 1.5% | sweetener |
| blackcurrant flavour | 20 mg | 1.2% | flavour |
| TOTAL | 1651 mg | 100.0% | |

(Mole ratio taste-masking compound: ibuprofen salt=8.6:1)

The contents of each sachet readily dissolved in 100 ml water and the objectionable taste and burning sensation normally associated with sodium ibuprofen were substantially undetectable in the resulting solution by most patients.

EXAMPLE 4

The procedure of Example 3 was repeated but using only 350 mg/sachet sodium bicarbonate. (Mole ratio taste-masking compound: ibuprofen salt=4.3:1.) The resulting aqueous solution had a taste which was identical to that of Example 3, ie. the burning sensation normally associated with sodium ibuprofen was substantially undetectable by most patients.

EXAMPLE 5

Non-effervescent, dry powdered sodium ibuprofen formulations were prepared as in Example 1, except that the amount of sodium bicarbonate included was variously 0, 81, 114, 175, 350, 525, 700, 1000, 1400 and 2000 mg/sachet.

(Mole ratio taste-masking compound: ibuprofen salt=0:1; 0.5:1; 0.7:1; 1.1:1; 2.2:1; 3.2:1; 4.3:1; 6.1:1; 8.6:1; and 12.3:1 respectively.)

The contents of each sachet readily dissolved in 100 ml water. On tasting the resulting solutions, it was found that the lowest level of sodium bicarbonate added (ie. 81 mg/sachet) did not mask the burning taste totally. Moreover, the highest level (ie. 2000 mg/sachet), whilst masking the taste of the ibuprofen salt, introduced an unacceptable taste itself. Optimal taste-masking occurred with bicarbonate added at 700 or 1000 mg/sachet.

EXAMPLE 6

Non-effervescent, dry powdered sodium ibuprofen formulations were prepared as in Example 1 except that instead of sodium carbonate there was used 19, 58, 97, 136, 194, 427, 621, 834, 1183, 1668 and 2385 mg/sachet of potassium bicarbonate.

(Mole ratios taste-masking compound: ibuprofen salt=0.1:1; 0.3:1; 0.5:1; 0.7:1; 1.0:1; 2.2:1; 3.2:1; 4.3:1; 6.1:1; 8.6:1; and 12.3:1 respectively)

The contents of each sachet readily dissolved in 100 ml water. On tasting the resultant solutions, it was found that the lowest level of potassium bicarbonate added (19 mg/sachet, did not mask the burning taste. Moreover, the higher levels (ie. 1668 mg/sachet and above), although masking the taste of the ibuprofen salt, introduced an unacceptable taste itself. Optimal taste-masking occurred at levels between 136 mg/sachet and 834 mg/sachet.

EXAMPLE 7

COMPARATIVE

A non-effervescent, dry powdered sodium ibuprofen formulation was prepared by mixing together the following ingredients and filling the mixture into sachets containing the equivalent of 400 mg free ibuprofen:

| Ingredient | mg/sachet | % w/w | purpose |
|---|---|---|---|
| sodium ibuprofen | 512 mg | 20.0 | active compound |
| ammonium bi-carbonate | 656 mg | 25.6 | taste modifier (and buffer) |
| dextrose | 1300 mg | 50.8 | bulking agent |
| sodium saccharin | 50 mg | 2.0 | sweetener |
| blackcurrant flavour | 40 mg | 1.6 | flavour |
| TOTAL | 2558 mg | 100.0% | |

The contents of each sachet readily dissolved in 100 ml water. However, the ammonium bicarbonate imparted an unpalatable taste to the aqueous solution.

EXAMPLE 8

A non-effervescent, dry powdered sodium ibuprofen formulation was prepared by mixing together the following ingredients and filling the mixture into sachets containing the equivalent of 400 mg free ibuprofen:

| Ingredient | mg/sachet | % w/w | purpose |
|---|---|---|---|
| sodium ibuprofen | 512 mg | 16.0 | active compound |
| trisodium citrate (dihydrate) | 600 mg | 18.7 | taste modifier (and buffer) |
| dextrose | 2000 mg | 62.5 | bulking agent |
| sodium saccharin | 50 mg | 1.6 | sweetener |
| blackcurrant flavour | 40 mg | 1.2 | flavour |
| TOTAL | 3202 mg | 100.0% | |

(Mole ratio taste-masking compound: ibuprofen salt=1.1:1)

The contents of each sachet readily dissolved in 100 ml water and the objectionable taste normally associated with sodium ibuprofen was substantially undetectable in the resulting solution by most patients. However, a slight burning sensation remained.

EXAMPLE 9

Comparative

The procedure of Example 8 was repeated but using either 1091 mg disodium citrate or 1079 mg monosodium citrate but in each case ibuprofen precipitated when the sachet contents were added to 100 ml water.

EXAMPLE 10

Non-effervescent, dry powdered sodium ibuprofen formulations were prepared as in Example 8, except that the amount of trisodium citrate included was variously 200, 400, 600, 800, 1200, 1700, 2400 and 3400 mg/sachet. The dihydrate citrate salt was used. (Mole ratio taste-masking compound: ibuprofen salt=0.4:1; 0.7:1; 1.1:1; 1.4:1; 2.1:1; 3.0:1; 4.2:1; and 6.0:1 respectively)

The contents of each sachet readily dissolved in 100 ml water. On tasting the resulting solutions, it was found that the lowest level of citrate added (ie. 200 mg/sachet) did not mask the burning taste. Moreover, the highest level (ie. 3400 mg/sachet), whilst masking the taste of the ibuprofen salt, introduced an unacceptable taste itself. Optimal taste-masking occurred when citrate was added at 400 or 600 mg/sachet.

EXAMPLE 11

A non-effervescent, dry powdered sodium ibuprofen formulation was prepared by mixing together the following ingredients and filling the mixture into sachets containing the equivalent of 400 mg free ibuprofen:

| Ingredient | mg/sachet | % w/w | purpose |
| --- | --- | --- | --- |
| sodium ibuprofen | 512 mg | 19.7 | active compound |
| sodium monohydrogen phosphate (anhydrous) | 700 mg | 26.9 | taste modifier (and buffer) |
| dextrose | 1300 mg | 50.0 | bulking agent |
| sodium saccharin | 50 mg | 1.9 | sweetener |
| blackcurrant flavour | 40 mg | 1.5 | flavour |
| TOTAL | 2602 mg | 100.0% | |

(Mole ratio taste-masking compound: ibuprofen salt = 2.5:1)

The contents of each sachet readily dissolved in 100 ml water and the objectionable taste normally associated with sodium ibuprofen was substantially undetectable in the resulting solution by most patients.

EXAMPLE 12

Non-effervescent, dry powdered sodium ibuprofen formulations were prepared as in Example 11, except that the amount of sodium monohydrogen phosphate included was variously 250, 500, 750, 1000, 1500 and 2000 mg/sachet. The anhydrous phosphate salt was used. (Mole ratio taste-masking compound: ibuprofen salt = 0.9:1; 1.8:1; 2.7:1; 3.6:1; 5.5:1; and 7.3:1 respectively.)

The contents of each sachet readily dissolved in 100 ml water. On tasting the resulting solutions, it was found that the lowest level of phosphate added (ie. 250 mg/sachet) did not mask the burning taste. Moreover, the highest level (ie. 2000 mg/sachet), whilst masking the taste of the ibuprofen salt, introduced an unacceptable taste itself. Optimal taste-masking occurred when phosphate was added at 750 or 1000 mg/sachet.

EXAMPLE 13

Comparative

The procedure of Example 11 was repeated but using 650 mg monosodium dihydrogen phosphate. Ibuprofen was precipitated when the sachet contents were added to 100 ml water.

EXAMPLE 14

Comparative

The procedure of Example 11 was repeated using 700 mg trisodium phosphate but the resultant solution was not tasted because the pH (12.1) was above the level (ca 10.5) at which it was considered there was a risk of damage to the oral mucosa.

Corresponding compositions containing sodium or potassium carbonate and sodium, potassium or ammonium hydroxide also were not tasted because of the high pH of
the resultant aqueous solution. The relevant data relating to these further compositions is as follows:

| Salt | mg/sachet | solution pH |
| --- | --- | --- |
| sodium carbonate | 440 | 10.7 |
| potassium carbonate | 572 | 10.9 |
| sodium hydroxide | 332 | 12.1 |
| potassium hydroxide | 465 | 12.8 |
| ammonium hydroxide | 530 | 11.2 |

In contrast to the above, the resultant solutions of Examples 1, 6, 7, 8 and 11 had the following pH:

| Example No. | pH |
| --- | --- |
| 1 | 8.3 |
| 6 | 8.5 |
| 7 | 8.5 |
| 8 | 9.0 |
| 11 | 9.6 |

EXAMPLE 15

A non-effervescent, dry powdered lysine ibuprofen formulation was prepared by mixing together the following ingredients and filling the mixture into sachets containing the equivalent of 400 mg free ibuprofen;

| Ingredient | mg/sachet | % w/w | purpose |
| --- | --- | --- | --- |
| lysine ibuprofen | 690 mg | 24.8 | active compound |
| sodium bicarbonate | 700 mg | 25.2 | taste modifier (and buffer) |
| dextrose | 1300 mg | 46.8 | bulking agent |
| sodium saccharin | 50 mg | 1.8 | sweetener |
| blackcurrant flavour | 40 mg | 1.4 | flavour |
| TOTAL | 2780 mg | 100.0% | |

(Mole ratio taste-masking compound: ibuprofen salt = 4.3:1)

The contents of each sachet readily dissolved in 100 ml water and the objectionable taste normally associated with lysine ibuprofen was substantially undetectable in the resulting solution by most patients. Thus, sodium bicarbonate effectively masked the burning sensation caused by lysine ibuprofen.

EXAMPLE 16

Comparative

A non-effervescent, dry powdered lysine ibuprofen formulation was prepared by mixing together the following ingredients and filling the mixture into sachets containing the equivalent of 400 mg free ibuprofen:

| Ingredient | mg/sachet | % w/w | purpose |
| --- | --- | --- | --- |
| lysine ibuprofen | 690 mg | 33.2 | active compound |
| dextrose | 1300 mg | 62.5 | bulking agent |
| sodium saccharin | 50 mg | 2.4 | sweetener |
| blackcurrant flavour | 40 mg | 1.9 | flavour |
| TOTAL | 2080 mg | 100.0% | |

The contents of each sachet readily dissolved in 100 ml water. Lysine ibuprofen was fully soluble in the water. Upon tasting, the solution gave rise to a strong, slightly delayed (20 to 30 seconds), burning sensation.

EXAMPLE 17

A taste trial of double blind fully randomized crossover design was conducted using 39 volunteers. Each volunteer was asked to drink 50 ml each of a control solution and a test solution of the following composition:

| Ingredient | Control mg/50 ml | Test mg/50 ml |
| --- | --- | --- |
| sodium ibuprofen | 256 mg | 256 mg |
| sodium bicarbonate | 0 mg | 350 mg |
| dextrose | 1000 mg | 650 mg |
| sodium saccharin | 25 mg | 25 mg |
| blackcurrant flavour | 20 mg | 20 mg |

(Mole ratio taste-masking compound: ibuprofen salt=0 for control) and 4.3:1 for test)

Twenty of the volunteers were given the control sample first and the remaining nineteen volunteers were given the test sample first. The order of presentation was randomized and neither the volunteers nor the trial administrators knew the identity of the samples. Two of the volunteers given the control sample first found the taste so unpleasant that they did not wish to continue with the test and no use was made of data from those volunteers.

The volunteers were asked to assess the following parameters relating to the taste of each sample and mark their assessment on visual analogue scales of 0-124 mm in length:

(a) taste on drinking;
(b) aftertaste;
(c) overall acceptability of the product.

For parameters (a) and (b), the volunteers were instructed to record only the sensory intensity of the taste and aftertaste rather than their subjective reaction to the sensation. The subjective reaction to the product was recorded separately as parameter (c). The t test result for each parameter was as follows:

| Parameter | t | probability | 95% confidence interval |
| --- | --- | --- | --- |
| (a) | −2.97 | 0.005 | −20.8 ± 14.2 |
| (b) | −3.86 | 0.0005 | −20.8 ± 10.9 |
| (c) | 2.98 | 0.005 | 18.8 ± 12.8 |

There was some variation in the scoring depending upon whether the control or test sample was taken first. However, as can be seen from the relevant data provided in Table I below, the order dependence was significant only for taste on drinking.

It is clear from the results of the taste trial reported above that addition of sodium bicarbonate to the control solution of sodium ibuprofen resulted in a significant improvement in the taste and overall acceptability of the product. It is particularly important to observe that there was a reduction in the severity of the perceived aftertaste.

TABLE I

| | | Control sample first | | | Test sample first | | |
| --- | --- | --- | --- | --- | --- | --- | --- |
| | | Control | test | difference | Control | test | difference |
| (a) | Taste on drinking | | | | | | |
| | Mean | 51.4 | 45.6 | −5.5 | 80.7 | 45.6 | −31.5 |
| | S.d. | 34.4 | 30.5 | | 20.5 | 28.0 | |
| (b) | Aftertaste | | | | | | |
| | Mean | 48.7 | 28.9 | −19.8 | 61.9 | 40.3 | −21.6 |
| | S.d. | 33.7 | 20.6 | | 28.3 | 34.1 | |
| (d) | Overall acceptability | | | | | | |
| | Mean | 83.9 | 94.3 | 10.4 | 60.1 | 86.7 | 26.6 |
| | S.d. | 28.4 | 21.0 | | 33.8 | 26.2 | |

EXAMPLE 18

A non-effervescent, dry powdered arginine ibuprofen formulation was prepared by mixing together the following ingredients and filling the mixture into sachets containing the equivalent of 400 mg free ibuprofen:

| Ingredient | mg/sachet | % w/w | purpose |
| --- | --- | --- | --- |
| arginine ibuprofen | 738 mg | 26.1 | active compound |
| sodium bicarbonate | 700 mg | 24.7 | taste modifier (and buffer) |
| dextrose | 1300 mg | 46.0 | bulking agent |
| sodium saccharin | 50 mg | 1.8 | sweetener |
| blackcurrant flavour | 40 mg | 1.4 | flavour |
| TOTAL | 2828 mg | 100.0% | |

(Mole ratio taste-masking compound: ibuprofen salt=4.3:1)

The contents of each sachet readily dissolved in 100 ml water and the objectionable taste normally associated with arginine ibuprofen was substantially undetectable in the resulting solution by most patients. Thus, sodium bicarbonate effectively masked the burning sensation caused by arginine ibuprofen.

EXAMPLE 19

Comparative

A non-effervescent, dry powdered arginine ibuprofen formulation was prepared by mixing together the following ingredients and filling the mixture into sachets containing the equivalent of 400 mg free ibuprofen:

| Ingredient | mg/sachet | % w/w | purpose |
| --- | --- | --- | --- |
| arginine ibuprofen | 738 mg | 34.7 | active compound |
| dextrose | 1300 mg | 61.1 | bulking agent |
| sodium saccharin | 50 mg | 2.3 | sweetener |
| blackcurrant flavour | 40 mg | 1.9 | flavour |
| TOTAL | 2128 mg | 100.0% | |

The contents of each sachet readily dissolved in 100 ml water. Arginine ibuprofen was fully soluble in the water. Upon tasting, the solution gave rise to a strong, slightly delayed significant burning sensation.

EXAMPLE 20

Non-effervescent, dry powdered sodium ibuprofen formulations were prepared as in Example 8, except that instead of trisodium citrate there was used 125, 251, 440, 691, 880, 1320, 1885, 2639 and 3771 mg/sachet of potassium citrate monohydrate.

(Mole ratio taste-masking compound: ibuprofen salt=0.2:1; 0.4:1; 0.7:1; 1.1:1; 1.4:1; 2.1:1; 3.0:1; 4.2:1; and 6.0:1 respectively.)

The contents of each sachet readily dissolved in 100 ml water. On tasting the resulting solutions, it was found that the lowest level of citrate added (ie. 125 mg/sachet) did not mask the burning taste. Moreover, the higher level (ie. 1885 mg/sachet and above), whilst masking the taste of the ibuprofen salt, introduced an unacceptable taste itself. Optimal taste-masking occurred when citrate was added at levels between 440 and 1320 mg/sachet.

EXAMPLE 21

Non-effervescent, dry powdered sodium ibuprofen formulations were prepared as in Example 11, except that instead of sodium monohydrogen phosphate, there was used 101, 169, 304, 607, 911, 1215, 1822, and 2463 mg/sachet of potassium monohydrogen phosphate.

(Mole ratio taste-masking compound ibuprofen salt=0.3:1; 0.5:1; 0.9:1; 1.8:1; 2.7:1; 3.6:1; 5.4:1; and 7.3:1 respectively.)

The contents of each sachet readily dissolved in 100 ml water. On tasting the resulting solutions, it was found that the lowest level of phosphate added (ie. 101 mg/sachet) did not mask the burning taste. Moreover, the highest level (ie. 2000 mg/sachet), whilst masking the taste of the ibuprofen salt, introduced an unacceptable taste itself. Optimal taste-masking occurred when phosphate was added at levels between 1215 and 1822 mg/sachet.

We claim:

1. A non-effervescent water-soluble composition comprising a water-soluble ibuprofen salt selected from the group consisting of potassium, sodium, arginine and lysine salts, and a sodium or potassium salt having a radical selected from the group consisting of bicarbonates, monohydrogen phosphates and tribasic citrates said sodium or potassium bicarbonate being present in a molar ratio of 1:4 to 12:1 with respect to the ibuprofen salt, said sodium or potassium tribasic citrate being present in a molar ratio of 1:3 to 3:1 with respect to the ibuprofen salt, and said sodium or potassium monohydrogen phosphate being present in a molar ratio of 3:4 to 7:1 with respect to the ibuprofen salt.

2. The composition according to claim 1, wherein the sodium or potassium salt is sodium or potassium bicarbonate.

3. The composition according to claim 1, wherein the sodium or potassium salt is sodium bicarbonate, monosodium phosphate or trisodium citrate.

4. The composition according to claim 3, wherein the sodium or potassium salt is sodium bicarbonate.

5. The composition according to claim 1, wherein the ibuprofen salt is an alkali metal ibuprofen salt.

6. The composition according to claim 2, wherein the sodium or potassium bicarbonate is present in a molar ratio of 3:4 to 9:1 with respect to the ibuprofen salt.

7. The composition according to claim 1, wherein the mono-hydrogen phosphate is present in a molar ratio of 5:2 to 6:1 with respect to the ibuprofen salt.

8. The composition according to claim 1, wherein the tribasic citrate is present in a molar ratio of 2:3 to 4:3 with respect to the ibuprofen salt.

9. A non-effervescent water-soluble composition comprising a water-soluble ibuprofen salt selected from the group consisting of potassium, sodium, azinine and lysine salts, and a sodium or potassium monohydrogen phosphate in a molar ratio of 3:4 to 7:1 with respect to the ibuprofen salt.

10. A non-effervescent water-soluble composition comprising a water-soluble ibuprofen salt selected from the group consisting of alkali metal salts and amino acid salts, and a sodium or potassium tribasic citrate in a molar ratio of 1:3 to 3:1 with respect to ibuprofen salt.

11. A method of masking the taste of a water-soluble ibuprofen salt selected from the group consisting of potassium, sodium, arzinine and lysine salts in a non-effervescent aqueous solution thereof by incorporating in said solution a taste-masking amount of a sodium or potassium salt having a radical selected from the group consisting of bicarbonate, monohydrogen phosphate and tribasic citrate.

12. The method according to claim 11, wherein the sodium or potassium salt is sodium or potassium bicarbonate.

13. The method according to claim 11, wherein the sodium or potassium salt is sodium bicarbonate, monosodium phosphate or trisodium citrate.

14. The method according to claim 13, wherein the sodium or potassium salt is sodium bicarbonate.

15. The method according to claim 11, wherein the ibuprofen salt is an alkali metal ibuprofen salt.

16. The method according to claim 12, wherein the sodium or potassium bicarbonate is present in a molar ratio of 1:4 to 12:1 with respect to the ibuprofen salt.

17. The method according to claim 16, wherein the sodium or potassium bicarbonate is present in a molar ratio of 3:4 to 9:1 with respect to the ibuprofen salt.

18. The method according to claim 11, wherein the sodium or potassium salt is an alkali metal mono-hydrogen phosphate and is present in a molar ratio of 3:4 to 7:1 with respect to the ibuprofen salt.

19. The method according to claim 18, wherein the mono-hydrogen phosphate is present in a molar ratio of 5:2 to 6:1 with respect to the ibuprofen salt.

20. The method according to claim 11, wherein the sodium or potassium salt is sodium or potassium salt tribasic citrate and is present in a molar ratio of 1:3 to 3:1 with respect to the ibuprofen salt.

21. The method according to claim 20, wherein the tribasic citrate is present in a molar ratio of 2:3 to 4:3 with respect to the ibuprofen salt.

* * * * *